United States Patent [19]
McGregor et al.

[11] Patent Number: 5,383,901
[45] Date of Patent: Jan. 24, 1995

[54] BLUNT POINT NEEDLES

[75] Inventors: Walter McGregor, Flemington; Semyon Shchervinsky, Whitehouse Station, both of N.J.

[73] Assignee: Ethicon, Inc., Somerville, N.J.

[21] Appl. No.: 138,680

[22] Filed: Oct. 18, 1993

[51] Int. Cl.⁶ ............................................. A61B 17/04
[52] U.S. Cl. .................................. 606/223; 606/224; 606/225
[58] Field of Search ............... 606/103, 222–225; 223/102–104; 401/216

[56] References Cited

U.S. PATENT DOCUMENTS

| | | |
|---|---|---|
| 3,162,176 | 12/1964 | Dombrow . |
| 3,708,234 | 1/1973 | Fukuda . |
| 3,904,297 | 9/1975 | Hori . |
| 3,945,735 | 3/1976 | Nakashiki et al. . |
| 4,116,569 | 9/1978 | Reed et al. . |
| 4,197,643 | 4/1980 | Burstone et al. . |
| 4,251,164 | 2/1981 | Nakagawa et al. . |
| 4,355,915 | 10/1982 | Kaji et al. . |
| 4,384,800 | 5/1983 | Dyama . |
| 4,513,747 | 4/1985 | Smith . |
| 4,660,559 | 4/1987 | McGregor et al. . |
| 4,672,734 | 6/1987 | Kawada et al. . |
| 4,789,263 | 12/1988 | Germann . |
| 4,799,484 | 1/1989 | Smith et al. . |
| 4,828,547 | 5/1989 | Sahi et al. . |
| 4,883,469 | 11/1989 | Glazier . |
| 4,883,471 | 11/1989 | Braginetz et al. . |
| 4,905,695 | 3/1990 | Bendel et al. . |
| 4,966,143 | 10/1990 | Meinershagen ............... 606/103 |
| 5,100,432 | 3/1992 | Matsutani . |
| 5,104,249 | 4/1992 | Elsner et al. . |
| 5,123,910 | 6/1992 | McIntosh ......................... 606/223 |
| 5,312,436 | 5/1994 | Coffey et al. ................... 606/228 |

FOREIGN PATENT DOCUMENTS

90/01349  2/1990  WIPO .

OTHER PUBLICATIONS

Abidin et al., Biomechanics of Curved Surgical Needle Bending, J. Biomed. Mater. Res. Appl. Biomaterials, vol. 23, No. A1, 129–143, (1989).
Bendel et al., Ophthalmic Needles, *Ophthalmology*, vol. 93, No. 9, (Sep. 1986).
McClung et al., Biomechanical Performance of Ophthalmic Surgical Needles, *Ophthalmology*, vol. 99, No. 2 (Feb. 1992).
Pavlovich, Lucas J., et al., A Synthetic Membrane for Testing Needle Penetration, *Journal of Applied Biomaterials*, vol. 4, 157–160 (1993).

*Primary Examiner*—Stephen C. Pellegrino
*Assistant Examiner*—Gary Jackson

[57] ABSTRACT

Blunt tip surgical needles which significantly reduce the probability of skin penetration of the gloved hand of an operator are disclosed. In one embodiment, the blunt tip needle includes a tip portion which terminates in a bulbous blunt tip. In another embodiment, the needle tip portion includes a ball socket and a ball rotatably disposed therein.

14 Claims, 2 Drawing Sheets

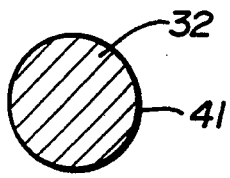
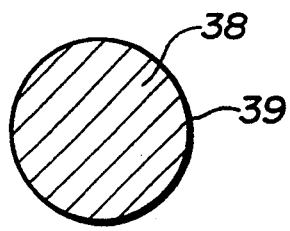
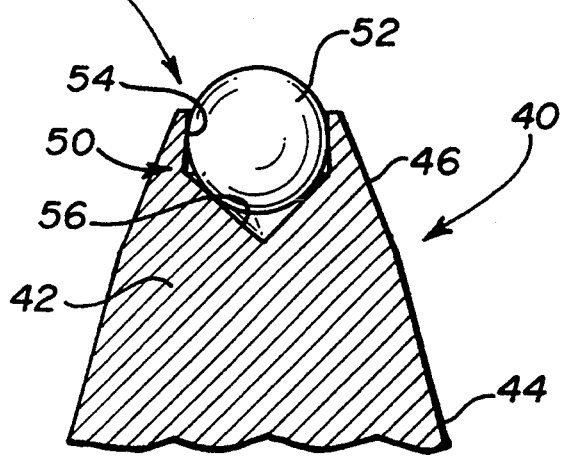
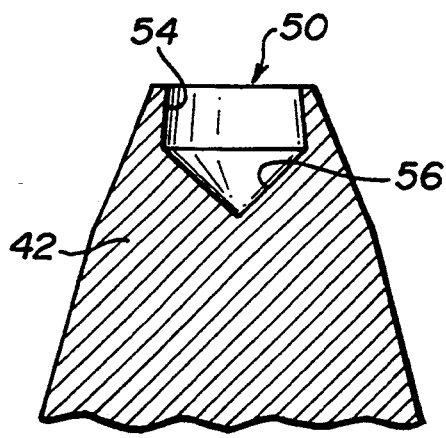
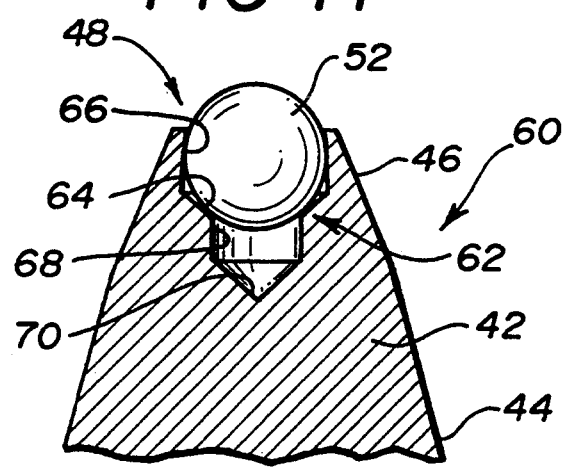

BLUNT POINT NEEDLES

BACKGROUND OF THE INVENTION

1. Field of the Invention

The present invention relates generally to surgical needles and, more particularly, to two blunt tip surgical needles wherein one needle has a bulbous tip and the other includes a ball tip that can roll on a surface and both needles decrease potential skin penetration of the gloved hand of an operator.

2. Description of the Prior Art

Everyone today is well aware of the severity of contracting Human Immunodeficiency Virus (HIV) and Acquired Immune Deficiency Syndrome (AIDS). The members of professions that must deal on a daily basis with the risk of coming in contact with people that do or may have HIV or AIDS are acutely aware of the severity. Members of the medical profession, especially surgeons, are in an extremely high risk position when performing operations. The knowledge that infectious diseases such as the AIDS virus can spread by an accidentally inflicted needle stick from a contaminated needle administered to the person having AIDS is the cause for much concern for the profession. These professionals are therefore taking every precaution to reduce the risks. For example, the use of double gloving, blunt tipped needles and gloves thickened at the fingers are known to reduce the rate of glove puncture. In addition, the use of forceps designed to grip both the tissue and needle more effectively and the use of staples for skin closure are also known to reduce the incidence of glove puncture.

Accordingly, there has been an increasing amount of activity in the area of surgical needle tip design. For example, U.S. Pat. No. 4,828,547 to Sahi et al. discloses a needle having a blunting member which is moveable from a retracted position to an extended position. In the retracted position, the blunting member does not interfere with the puncture tip of the needle. In the extended position, the blunting member extends beyond the puncture tip and therefor acts as a guard against accidental needle sticks. Further examples of shield or guard type assemblies for syringe needles are disclosed in U.S. Pat. Nos. 4,883,469 to Glazier and 4,883,471 to Braginetz et al.

The devices disclosed above are useful for hypodermic syringe needles which are disposed of after a single stick. This design would not be practical for use with surgical needles since such needles must make repeated sticks into the body.

U.S. Pat. No. 5,123,910 to Mcintosh discloses a tapered needle tip having a circular cross-section and terminating in a blunt head. The blunt head has a part spherical or other curved shape with no sharp edge surfaces. However, since no part of the curved tip is larger than the smallest circumference of the tapered tip portion and the blunt tip cannot roll on a surface to be contacted, this needle still can penetrate the gloved hand of an operator. Thus, although this blunt tip needle is an improvement over a conventional sharp point needle, it does not significantly reduce the probability of skin penetration of a gloved hand. Thus, there is a need to develop an improved surgical needle for use in suturing non-cutaneous and friable soft tissues of the body while at the same time significantly reducing the probability of skin penetration of the gloved hand of an operator.

SUMMARY OF THE INVENTION

The present invention is directed to blunt tip surgical needles which significantly reduce the probability of skin penetration of the gloved hand of an operator thereby decreasing potential transmission of all infectious agents. In one embodiment of the present invention, the needle includes a tip portion which terminates in a bulbous blunt tip. The provision of the bulbous tip improves upon prior art blunt tip needles in that the needle of the present invention is less likely to penetrate the glove and skin of the user.

In one embodiment of the bulbous tip needle of the present invention, the needle includes a tip portion and a contiguous blunt tip at a distal end thereof. The tip portion can have a generally uniform cross-section throughout its length or have a cross-section which decreases progressively toward the distal end. The cross-sectional perimeter of the blunt tip is greater than the cross-sectional perimeter of a distal end of the tip portion. The bulbous blunt tip blends smoothly with the outer surface of the distal end of the tip portion such that there are no sharp edges at the needle tip. By utilizing a larger radius tip on a smaller diameter needle, the needle of the present invention is suitable for use in suturing non-cutaneous tissues of the body while at the same time significantly reducing the probability of skin penetration of the gloved hand of an operator.

As an example, the tip portion can have a circular cross-section and the bulbous tip can be substantially spherical. However, this configuration is not critical to the present invention and the tip portion and blunt tip can have a wide variety of shapes so long as the perimeter of the blunt tip is greater than the perimeter of the distal end of the tip portion. In addition, for any shape of the blunt tip, the tip portion can have any one of variety of conventional shapes such as circular, square, rectangular, triangular or flat-pressed circular.

In another embodiment of the present invention, the needle tip portion includes a ball socket at its distal end for the rotable retention of a ball and a ball rotatably retained within the socket. The bottom of the ball socket includes a concave shaped ball seat. In an alternative embodiment, the ball socket includes a circumferentially inwardly inclined support surface disposed between first and second bores. In this embodiment, the ball rotatably contacts an upper rim of the first bore, a lower perimeter of the support surface and an upper rim of the second bore.

In both of the embodiments, the ball makes the initial contact with the surface of the tissue to be penetrated. When the ball contacts the surface of a plastic glove, the ball will initially roll on the surface and not penetrate thereby allowing the surgeon to quickly withdraw the needle without penetrating through the glove and into the skin. Thus, the provision of the ball at the needle tip improves upon the prior art blunt tip needles in that the present needle is less likely to penetrate the glove and skin of the user. On the other hand the ball will not roll as freely when in contact with the tissue and can penetrate the tissue with the proper force applied to perform the suturing function. Thus, the rolling ball needle of the present invention provides protection against the unintentional stick of the gloved hand of an operator while not adversely effecting the surgeon's ability to suture tissue.

As a result of having a bulbous blunt tip or a rotatable ball tip, the needles of the present invention are a significant improvement over conventional sharp point needles and prior art blunt tip needles. The improved blunt tip surgical needles of the present invention are suitable for use in suturing soft-non-cutaneous or friable body tissues, as well as other types of tissue, while providing increased protection against an unintended stick of the gloved hand of an operation.

BRIEF DESCRIPTION OF THE DRAWINGS

FIG. 7 is a cross-sectional view taken along the lines 7—7 in FIG. 6.

FIG. 8 is a cross-sectional view taken along the lines 8—8 in FIG. 6.

FIG. 9 is a cross-sectional view of the tip portion of a further embodiment of a surgical needle according to the present invention.

FIG. 10 is a cross-sectional view of the tip portion of FIG. 9 without the rotatable ball.

FIG. 11 is a cross-sectional view of the tip portion of another embodiment of a surgical needle of the present invention.

DETAILED DESCRIPTION OF THE INVENTION

Figure 1:
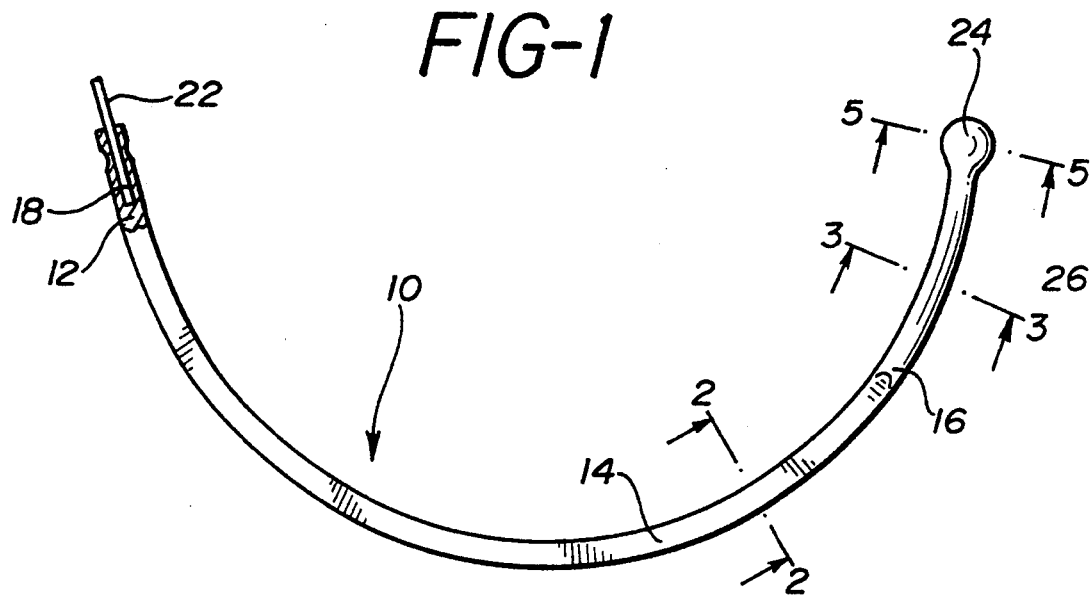
FIG. 1 is a perspective view of one embodiment of a surgical needle of the present invention.

Referring to the drawings in FIGS. 1-5, there is shown one embodiment of the blunt tip surgical needle 10 of the present invention. The needle 10 includes a suture mounting portion 12, a contiguous main body portion 14 having a generally uniform cross-sectional area throughout an entire length thereof and a contiguous tip portion 16.

The suture mounting portion 12 is straight and has a hole 18 extending from a proximal end face of the suture needle along an axis thereof. The length of the suture mounting portion 12 is generally equal to or slightly greater than the length of the hole 18. A suture 22 is inserted at one end portion into hole 18 and then the suture mounting portion 12 is deformed or compressed to hold the suture 22.

Figure 2:
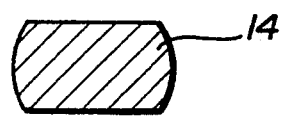
FIG. 2 is a cross-sectional view taken along lines 2—2 in FIG. 1.

The cross-sectional shape of the main body portion 14 can have a wide variety of conventional shapes including circular, square, rectangular and triangular. However, in order to provide stability and control of needle 10 during use, the main body portion 14 can have a flat pressed circular cross-section as shown in FIG. 2. In the needle 10, the main body portion 14 and the tip portion 16 are curved and can possess a constant radius of curvature. This configuration is, however, not critical to the present invention and body portion 14 and tip portion 16 can therefore assume any straight and/or curved configuration which is considered suitable for the particular purpose that is intended.

Figure 3:
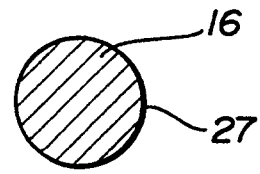
FIG. 3 is a cross-sectional view taken along lines 3—3 in FIG. 1.
Figure 4:
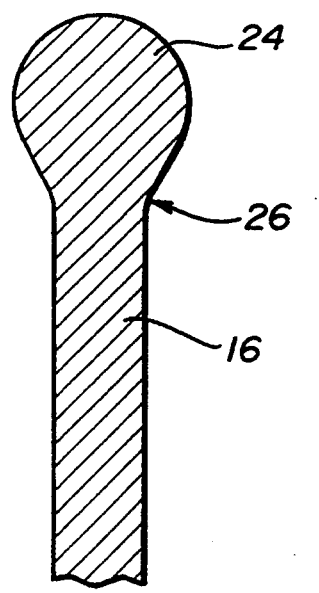
FIG. 4 is a cross-sectional view of the tip portion of the needle of FIG. 1.

Referring to FIGS. 1, 3 and 4, there is shown one embodiment of a blunt tip surgical needle 10 according to the present invention. The needle 10 exhibits a generally uniform cross-sectional shape over main body portion 14 and the contiguous tip portion 16 and terminates in a bulbous blunt tip 24. As shown in FIG. 3, the cross-sectional shape of tip portion 16 can be, for example, circular.

Figure 5:
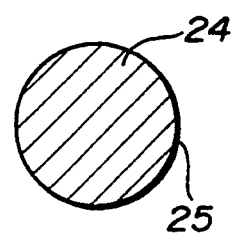
FIG. 5 is a cross-sectional view taken along lines 5—5 in FIG. 1.

The blunt tip 24 can have a substantially spherical shape as shown in FIGS. 1 and 4. Referring to FIGS. 3 and 5, the cross-sectional perimeter 25 of the widest part of the blunt tip 24 should be greater than the cross-sectional perimeter 27 of the distal end of the tip portion 16. In the illustrative example of FIGS. 3-5, the diameter of tip 24 should be greater than the diameter tip portion 16 to provide a bulbous blunt tip 24. The shape of needle 10 at the tip makes a smooth transition at 26 from the tip portion 16 to blunt tip 24 such that there are no sharp edges or discontinuities at tip 24.

By utilizing bulbous blunt tip 24, the penetration force of needle 10 needed to penetrate the gloved hand of an operator is significantly increased as compared to conventional sharp point needles and prior art blunt tip needles. Consequently, needle 10 significantly decreases the probability of skin penetration of the gloved hand of an operator. In addition, the needle 10 has the advantage that a larger diameter tip 24 can be made on a smaller diameter needle body. This feature allows needle 10 to be easily drawn through an opening in the tissue being sutured once the needle tip has penetrated the tissue since the hole made by tip 24 will be larger than the needle body.

Figure 6:
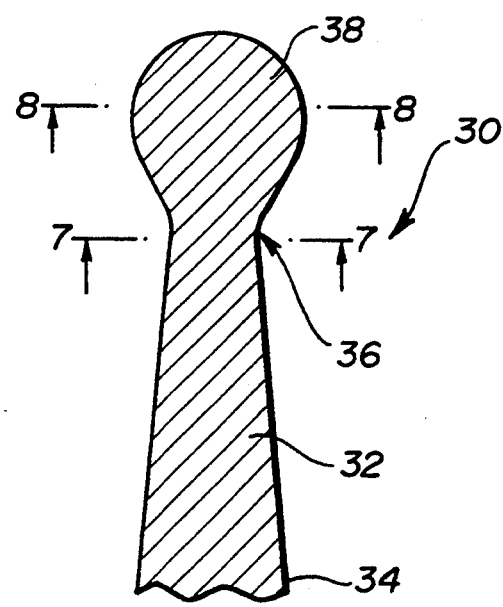
FIG. 6 is a cross-sectional view of the tip portion of another embodiment of a surgical needle of the present invention.

Referring to FIGS. 6-8, there is shown another embodiment of a surgical needle 30 according to the present invention. In this embodiment, the needle tip portion 32 has a circular cross-sectional shape which decreases progressively from its proximal end 34 to its distal end 36. The tip portion 32 terminates in a bulbous blunt tip 38 which is configured to permit piercing of non-cutaneous or friable soft tissues of the body while preventing skin penetration of the gloved hand of an operator. Due to the taper shape of tip portion 32, needle 30 will have a thicker tip portion and a thicker body portion than needle 10. As a result, the needle 30 provides more strength to penetrate tissue which is being sutured without bending or breaking. In addition, the thicker tip and body portions of needle 30 provide more stability in that the body portion can be more easily grasped and held in a suitable needle holding instrument.

As shown in FIG. 6, the blunt tip 38 can have a substantially spherical shape. As shown by comparing FIGS. 7 and 8, the cross-sectional perimeter 39 of the widest part of the blunt tip 38 should be greater than the cross-sectional perimeter 41 of the distal end 36 of tip portion 32. The blunt tip 38 blends smoothly with the outer surface of the distal end 36 of tip portion 32 such that there are no sharp edges or discontinuities at tip 38.

It should be understood by those skilled in the art of the present invention that although the tip portion was described with a circular cross-sectional shape and the blunt tips 24 and 38 with a spherical shape, these configurations are not critical to the present invention. The tip portion and the blunt tip can have a wide variety of shapes so long as the width of the blunt tip is greater than the width of the distal end of the tip portion. For example, the blunt tips 24 and 38 can have an elliptical or oval dome shape with a cross-sectional perimeter at its widest area greater than the cross-sectional perimeter of the distal end of the respective tip portions. In addition, for any shape of the blunt tip, the tip portion can have any one of the shapes described above, such as a circular, square, rectangular, triangular and flat pressed circular.

Blunt tip 24 has a cross-sectional diameter at its widest area from about 25% to about 300% larger than the diameter of needle tip portion 16. Blunt tip 38 has a cross-sectional diameter at its widest area from about 25% to about 300% larger than the narrowest diameter of needle tip portion 32. The diameter of the main body 14 of the needles can be in the range of about 0.020" to 0.050".

The needles 10 and 30 are rigidly formed of a suitable material such as surgical grade steel, plastic material and/or combinations of steel and plastic.

Referring to FIG. 9, there is shown another embodiment of a surgical needle 40 according to the present invention. The needle tip portion 42 can have a circular cross-sectional shape which decreases progressively from its proximal end 44 to its distal end 46. The tip portion 42 terminates in a blunt tip 48. The blunt tip 48 comprises a ball socket 50 adapted to hold a freely rotatable ball 52. The ball socket 50 at its outer tip has a ball clasping bore 54 and a contiguous conical shaped ball seat 56 as shown in FIG. 10. The ball 52 is assembled in place by fitting it through the open end of the bore 54 and onto the ball seat 56 and crimping the rim of the bore 54 at its extremity so that it clasps the ball 52 and prevents it from dropping out. The ball 52 can have a diameter ranging from about 0.005" to 0.060".

FIG. 11 shows a further embodiment of a surgical needle 60 of the present invention. The ball socket 62 is adapted to retain the freely rotatable ball 52. In this embodiment, the ball socket 62 includes a circumferentially inwardly inclined support surface 64 disposed between and contiguous with a first bore 66 and a second bore 68. The ball 52 is in contact with an upper rim of the first bore, a lower perimeter of surface 64 and an upper rim of the second bore 68. A contiguous conical shaped portion 70 extends from a lower part of the second bore 68. The first bore 66 is a ball clasping bore and is crimped at its rim to rotatably contain ball 52 and prevent it from dropping out.

It should be understood by those skilled in the art of the present invention that the shape and configuration of the ball holder, socket and ball seat are not critical to the present invention and can therefore assume any configuration which allows the ball 52 to be freely rotatable. For example, in addition to the embodiments described above, ball seat 56 can have an inclined concave surface or an open spherical surface.

The curved surface of ball 52 of the needles of the present invention significantly decrease the probability of skin penetration of the gloved hand of an operator as compared to conventional sharp point needles and prior art blunt tip needles. In addition, the needles 40 and 60 provide additional protection against an unintentional stick of the gloved hand of an operator in that when the ball 52 contacts the surface of a latex glove, the ball will roll on the surface without penetrating it. This allows the surgeon to quickly withdraw the needle without penetrating through the glove and into the skin. The needles 40 and 60 have the further advantage that the ball 52 can be made of a hard material such as carbide while the needle body 42 can be made of any one of the steel materials described above with regard to needles 10 and 30. This will provide sufficient structural integrity to the ball 52 to effectively penetrate non-cutaneous tissue without the ball being damaged or otherwise deformed.

The needles of the present invention are suitable for use in suturing the liver, kidney, heart, muscle and fascia, adipose pericostal tissue and other non-cutaneous soft tissues of the body, as well as other types of tissue, while simultaneously decreasing the probability of skin penetration of the gloved hand of an operator and operating personnel such as surgeons, surgeons' assistants, scrube and circulating nurses.

While the invention has been particularly shown and described with respect to illustrative and preferred embodiments thereof, it will be understood by those skilled in the art that the foregoing and other changes in form and details may be made therein without departing from the spirit and scope of the invention which should be limited only by the scope of the appended claims.

What is claimed is:

1. A surgical needle comprising:
    a tip portion having a proximal end and a distal end, said distal end having a cross-sectional perimeter wherein said tip portion has a cross-sectional area which decreases progressively toward said distal end;
    a blunt tip contiguous with said distal end of said tip portion, said blunt tip having a cross-sectional perimeter which is greater than said cross-sectional perimeter of said distal end of said tip portion;
    a suture mounting portion having a hole to which a suture is to be attached, said suture mounting portion extending from the proximal end of the needle; and
    a body portion which is disposed between and contiguous with said suture mounting portion and said tip portion, wherein said body portion has a generally uniform cross-sectional area throughout an entire length thereof,
wherein said cross-section of said tip portion is circular and said blunt tip has a substantially spherical shape.

2. The surgical needle according to claim 1, wherein said needle has an overall curved shape with a constant radius of curvature.

3. The surgical needle according to claim 2, wherein said cross-sectional area of said body portion has a shape selected from the group consisting of circular, square, rectangular, triangular and flat pressed circular.

4. The surgical needle according to claim 1, wherein said cross-sectional perimeter of said blunt tip has a diameter from about 25% to about 300% greater than the diameter of the cross-sectional perimeter of said distal end of said tip portion.

5. A surgical needle comprising:
    a tip portion having a proximal end and a distal end, said distal end having a ball socket for the rotatable retention of a ball, and
    a ball rotatably retained within said ball socket.

6. The surgical needle according to claim 5, wherein the ball socket includes a first bore at an upper portion of the ball socket.

7. The surgical needle according to claim 6, wherein said ball socket further includes a second bore and a circumferential inwardly inclined support surface disposed between and contiguous with the first and second bores.

8. The surgical needle according to claim 7, further including a conical shaped lower surface extending from a lower perimeter of said second bore.

9. The surgical needle according to claim 6, wherein said ball socket further includes a concave shaped ball seat at a bottom of the ball socket and continuous with said first bore.

10. The surgical needle according to claim 9, wherein the ball seat has a shape selected from the group consisting of conical and spherical.

11. The surgical needle according to claim 10, further including a suture mounting portion have a hole to which a suture is to be attached, and a body portion which is disposed between and contiguous with said suture mounting portion and said tip portion.

12. The surgical needle according to claim 11, wherein said body portion has a generally uniform cross-sectional area throughout an entire length thereof.

13. The surgical needle according to claim 12, wherein said needle has an overall curved shape with a constant radius of curvature.

14. The surgical needle according to claim 13, wherein said cross-sectional area of said body portion has a shape selected from the group consisting of circular, square, rectangular, triangular and flat pressed circular.

* * * * *